(12) United States Patent
Christoph (10) Patent No.: US 11,432,610 B2
(45) Date of Patent: Sep. 6, 2022

(54) ACTIVE NOISE CONTROL IN A HELMET

(71) Applicant: HARMAN BECKER AUTOMOTIVE SYSTEMS GMBH, Karlsbad (DE)

(72) Inventor: Markus Christoph, Straubing (DE)

(73) Assignee: Harman Becker Automotive Systems GmbH, Karlsbad (DE)

(*) Notice: Subject to any disclaimer, the term of this patent is extended or adjusted under 35 U.S.C. 154(b) by 0 days.

(21) Appl. No.: 15/380,297

(22) Filed: Dec. 15, 2016

(65) Prior Publication Data

US 2017/0178616 A1    Jun. 22, 2017

(30) Foreign Application Priority Data

Dec. 16, 2015 (EP) .................................... 15200376

(51) Int. Cl.
  *G10K 11/16* (2006.01)
  *A42B 3/16* (2006.01)
  (Continued)

(52) U.S. Cl.
  CPC .............. *A42B 3/166* (2013.01); *A42B 3/303* (2013.01); *A42B 3/306* (2013.01); *G10K 11/162* (2013.01);
  (Continued)

(58) Field of Classification Search
  CPC ... G10K 2210/1081; G10K 2210/3026; G10K 2210/3027; G10K 2210/3046;
  (Continued)

(56) References Cited

U.S. PATENT DOCUMENTS 5,913,412 A * 6/1999 Huber .................... A42B 3/122
                                                                      2/413
6,078,672 A   6/2000 Saunders et al.
(Continued)

FOREIGN PATENT DOCUMENTS

CN    2414640 Y    1/2001
CN    1624762 A    6/2005
(Continued)

OTHER PUBLICATIONS

Castañé-Selga et al., "Active Noise Hybrid Time-Varying Control for Motorcycle Helmets", IEEE Transactions on Control Systems Technology, vol. 18, No. 3, May 2010, pp. 602-612.
(Continued)

*Primary Examiner* — Katherine A Faley
(74) *Attorney, Agent, or Firm* — Brooks Kushman P.C.

(57) ABSTRACT

Exemplary noise reducing methods and systems are configured to acoustically reproduce two electrical noise reducing signals at two opposing positions in a helmet; to pick up sound at positions in the vicinity of the positions where the noise reducing signals are reproduced; and to generate the two noise reducing signals from error-signals and reference-signals. For each noise reducing signal, the corresponding error-signal is generated from the sound picked-up at the same position where the respective noise reducing signal is reproduced; and the reference-signal is generated from the sound picked-up at the position where the respective other noise reducing signal is reproduced.

19 Claims, 6 Drawing Sheets

(51) Int. Cl.
*H04R 1/10* (2006.01)
*G10K 11/178* (2006.01)
*A42B 3/30* (2006.01)
*G10K 11/162* (2006.01)
*A61F 11/14* (2006.01)

(52) U.S. Cl.
CPC .. *G10K 11/17857* (2018.01); *G10K 11/17861* (2018.01); *G10K 11/17881* (2018.01); *H04R 1/1083* (2013.01); *A61F 2011/145* (2013.01); *G10K 2210/1081* (2013.01); *G10K 2210/3026* (2013.01); *G10K 2210/3027* (2013.01); *G10K 2210/3046* (2013.01); *H04R 2410/05* (2013.01); *H04R 2460/01* (2013.01)

(58) Field of Classification Search
CPC ............... G10K 11/175; G10K 11/178; G10K 11/1786; G10K 11/1788; A61F 2011/145; H04R 2460/01
USPC ................................................ 381/71.6, 71.7
See application file for complete search history.

(56) References Cited

U.S. PATENT DOCUMENTS

| | | | | |
|---|---|---|---|---|
| 7,466,838 | B1* | 12/2008 | Moseley | G10K 11/178 381/370 |
| 2007/0119538 | A1* | 5/2007 | Price | A42B 3/06 156/242 |
| 2008/0250550 | A1* | 10/2008 | Bologna | A42B 3/20 2/425 |
| 2010/0150367 | A1* | 6/2010 | Mizuno | G10K 11/178 381/71.6 |
| 2010/0183182 | A1 | 7/2010 | Grandt et al. | |
| 2011/0044464 | A1 | 2/2011 | Sapiejewski et al. | |
| 2013/0133128 | A1 | 5/2013 | Hein et al. | |
| 2014/0189937 | A1* | 7/2014 | Pietrzak | A42B 3/062 2/411 |

FOREIGN PATENT DOCUMENTS

| | | |
|---|---|---|
| CN | 101516051 A | 8/2009 |
| CN | 103428608 A | 12/2013 |
| CN | 104473719 A | 4/2015 |
| CN | 204392507 U | 6/2015 |
| EP | 1075164 A2 | 2/2001 |
| EP | 2086250 A1 | 8/2009 |
| JP | H08113815 A | 5/1996 |
| JP | 2007002393 A | 1/2007 |
| WO | 2006008492 A2 | 1/2006 |

OTHER PUBLICATIONS

European Search Report for Application No. 15200376.0, dated Jun. 22, 2016, 7 pages.
Extended European Search Report for Application No. 15200376.0, dated Aug. 19, 2016, 14 pages.
Raghunathan, Kishan P. et al., "Active Noise Control for Motorcycle Helmets", Aug. 9, 2010, 5 pgs.
Rui-Ming, Li, "The Application of Adaptive Active Noise Control Theory in Tank Helmet", May 2013, 58 pgs.
Tang, Hong et al., "Design and Simulation of Adaptive Active Noise Control System for Aircraft Helmet", Aircraft Design, Oct. 2011, 4 pgs., vol. 31 No. 5.
Chinese Office Action for Application No. 201611144144.X filed Dec. 13, 2016, dated Apr. 20, 2021, 23 pgs.
Chinese Office Action for Application No. 201611144144.X filed Dec. 13, 2016, dated Jul. 30, 2021, 16 pgs.
Chinese Office Action for Application No. 201611144144.X filed Dec. 13, 2016, dated Nov. 26, 2021, 15 pgs.
European Office Action for Application No. 15200376.0 filed Dec. 16, 2016, dated Jun. 19, 2018. 8 pgs.

* cited by examiner

FIG 11

ACTIVE NOISE CONTROL IN A HELMET

CROSS-REFERENCE TO RELATED APPLICATIONS

This application claims priority to EP application Serial No. 15200376.0 filed Dec. 16, 2015, the disclosure of which is hereby incorporated in its entirety by reference herein.

TECHNICAL FIELD

The disclosure relates to a system and method (generally referred to as a "system") for active noise control in a helmet.

BACKGROUND

A motorcyclist's ability to hear while riding is a critical safety factor in the modern environment. Unfortunately, a motorcyclist's hearing may be impeded by engine noise, wind noise and helmet design, among other things. High noise levels, such as those experienced by motorcyclists, may increase fatigue, impair reaction times and impair attention, effectively reducing the safety of the motorcyclists and those around him or her. Moreover, high intensity noise over long periods of time may have long-term consequences on a motorcyclist's hearing ability. At highway speeds, noise levels may easily exceed 100 dB when wearing a traditional helmet. This is particularly troublesome for daily motorcyclists as well as occupational motorcyclists, such as police officers. To combat the noise, some motorcycle helmets use sound deadening material around the area of the ears. Other motorcyclists may opt to use earplugs to reduce noise and prevent noise induced hearing loss. Another way to reduce noise are built-in active noise cancellation systems which, however, also exhibit some drawbacks.

SUMMARY

An exemplary noise reducing helmet includes a shell, an isolation layer disposed in the shell and having two receptacles at opposing positions, two loudspeakers disposed in the two receptacles, two microphones disposed in the vicinity of the two loudspeakers, and an active noise control module having two channels each with an error-signal input, a reference-signal input and an output. The outputs of the two channels are electrically coupled to the two loudspeakers, the error-signal input of each channel is electrically coupled to the microphone in the vicinity of the loudspeaker that is electrically coupled to the output of the same channel, and the reference-signal input of each channel is electrically coupled to the microphone in the vicinity of the loudspeaker that is electrically coupled to the output of the respective other channel.

An exemplary noise reducing method includes: acoustically reproducing two electrical noise reducing signals at two opposing positions in a helmet; picking up sound at positions in the vicinity of the positions where the noise reducing signals are reproduced; and generating the two noise reducing signals from error-signals and reference-signals. For each noise reducing signal, the corresponding error-signal is generated from the sound picked-up at the same position where the respective noise reducing signal is reproduced; and the reference-signal is generated from the sound picked-up at the position where the respective other noise reducing signal is reproduced.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

In a conventional hybrid ANC system, which may be a combination of a feedback (also known as closed loop) ANC sub-system and feed-forward (also known as open loop) ANC sub-system, each of the sub-systems has its own error-microphone. Such hybrid ANC systems are often used in ANC headphones, but cannot usually be used for helmets. While it is not a problem to install an error microphone for the feedback ANC sub-system, for example, close to the secondary source such as a loudspeaker, at each side of the helmet, it is difficult to find a suitable position for the feed-forward sub-system's error microphone. The outer surface of the helmet would be a natural position for such a sensor, but this position is not advisable since it may lead to overload of the feed-forward sub-system's error microphone due to the given harsh acoustical environmental conditions, particularly when the helmet is worn while driving a motorbike. Noise affecting a motorcyclist may have many sources, such as engine noise, road noise, other vehicle noise and wind noise. As the speed of a motorcycle increases, typically the most prominent source of noise is wind. This effect increases dramatically as speed increases.

A helmet may comprise several layers, including a shell, a shock-absorbing layer, and a comfort layer. A helmet's shell is the outermost layer and is typically made from resilient, water-resistant materials such as plastic and fiber composites. A helmet's shock-absorbing layer, which is its primary safety layer, may be made out of a rigid, but shock-absorbing material such as expandable polystyrene foam. Although not typical, a helmet's fire-proof layer may be integrated and made of a closed-cell material such as vinyl-nitrile, which is both fire and water resistant. Further, this layer may have sound and thermo-insulating qualities and may be alternatively referred to as an acoustic layer. Finally, a helmet's comfort layer may be made of a soft material meant to contact with a motorcyclist's skin, such as cotton or other fabric blends as are known in the art. Other layers may be present as well, and some of the aforementioned layers may be omitted or combined.

Figure 1:
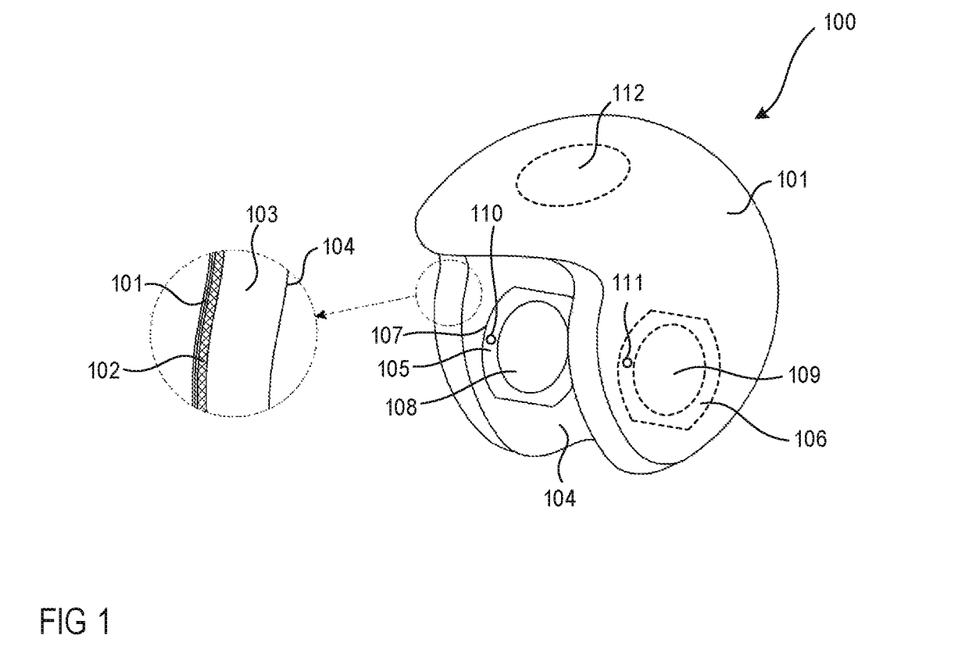
FIG. 1 is a perspective view of a motorcycle helmet with an active noise control system.

FIG. 1 is a perspective view of a motorcycle helmet 100. The helmet 100 comprises an outer shell 101, an acoustic layer 102, a foam layer 103, a comfort layer 104, and an optionally passive noise reduction system (not shown). The helmet 100 further comprises ear-cups 105 and 106 which are mounted on each inner side of the helmet 100 where the ears of a user will be when the helmet 100 is worn by the user. Note that in FIG. 1 only one ear-cup 105 is visible. However, an identical ear-cup 106, shown in broken lines, is also present on the opposite side of the helmet 100.

As is shown in FIG. 1, the ear-cup 105 is (and so is ear-cup 106) isolated from the shell 101 of the helmet 100 by an isolation mount 107. The isolation mount 107 may be made of a vibration dampening material. The vibration dampening material may prevent shell 101 vibrations from reaching a user's ear and thus may decrease the user's perception of those vibrations as noise. Thus, by mounting the ear-cup 105 to something other than the shell 101 of the helmet 100, and decoupling it from rigid materials that easily transmit vibrations, noise transmitted to the ear-cup 105 may be reduced.

Each ear-cup 105, 106 may partly embrace, for example, a loudspeaker 108, 109 or any other type of sound driver or electro-acoustic transducer or a group of loudspeakers, built into the ear-cup 105, 106. Additionally, the helmet 100 may include acoustic sensors such as microphones 110 and 111 that sense noise and actively cancel them in conjunction with loudspeakers 108 and 109 in each ear-cup 105 and 106. The microphones 110 and 111 are disposed in the vicinity of the loudspeakers 108 and 109, which means in the present example that they are disposed on the same side of the helmet 100 as the respective loudspeaker 108, 109 since the loudspeakers 108 and 109 are disposed at opposing positions inside the helmet 100. The loudspeakers 108 and 109 and the microphones 110 and 111 are connected to an active noise controller 112. In this way, the benefits of the optional passive noise reduction system may be combined with an active noise reduction system. The active noise controller 112 may be partly or completely mounted within the shell 101 of helmet 100 and may be isolated from the shell 101 by vibration dampening material. Alternatively, the active noise controller 112 is completely disposed outside the helmet 100 and the loudspeakers 108, 109 and the microphones 110, 111 are linked via a wire-line or wireless connection to the active noise controller 112. Furthermore, the active noise controller 112—regardless of where the active noise controller 112 is disposed—may be linked via a wire-line or wireless connection to an audio signal bus system and/or a data bus system (both not shown in FIG. 1).

Figure 2:
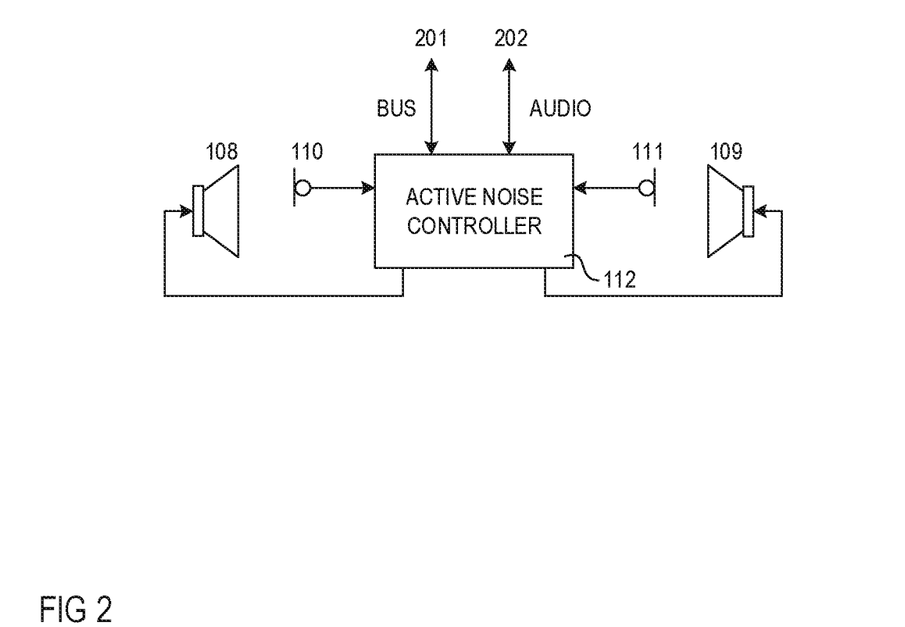
FIG. 2 is a block diagram illustrating the signal flow in the helmet shown in FIG. 1.

FIG. 2 shows the active noise controller 112 used in the helmet 100 shown in FIG. 1. Microphones 110 and 111 provide to the active noise controller 112 electrical signals that represent the sound picked up by the microphones 110 and 111 at their respective positions. The active noise controller 112 processes the signals from the microphones 110, 111, and produces signals therefrom that are supplied to the loudspeakers 108 and 109. The active noise controller 112 may additionally transmit or receive data and/or audio signals via data bus 201 and/or audio signal bus 202.

In the exemplary hybrid system shown in FIG. 1, microphones 110 and 111 are disposed inside the helmet 100 at the same curved plane as secondary sources, for example, loudspeakers 108 and 109, and may be, furthermore, be arranged in such a way that they face the opening (front side) of the helmet 100 and in the direction where the noise source resides. These microphone positions, although within the helmet 100, still allow to use a feed-forward system based on the same microphones as the feedback ANC-systems use.

Figure 3:
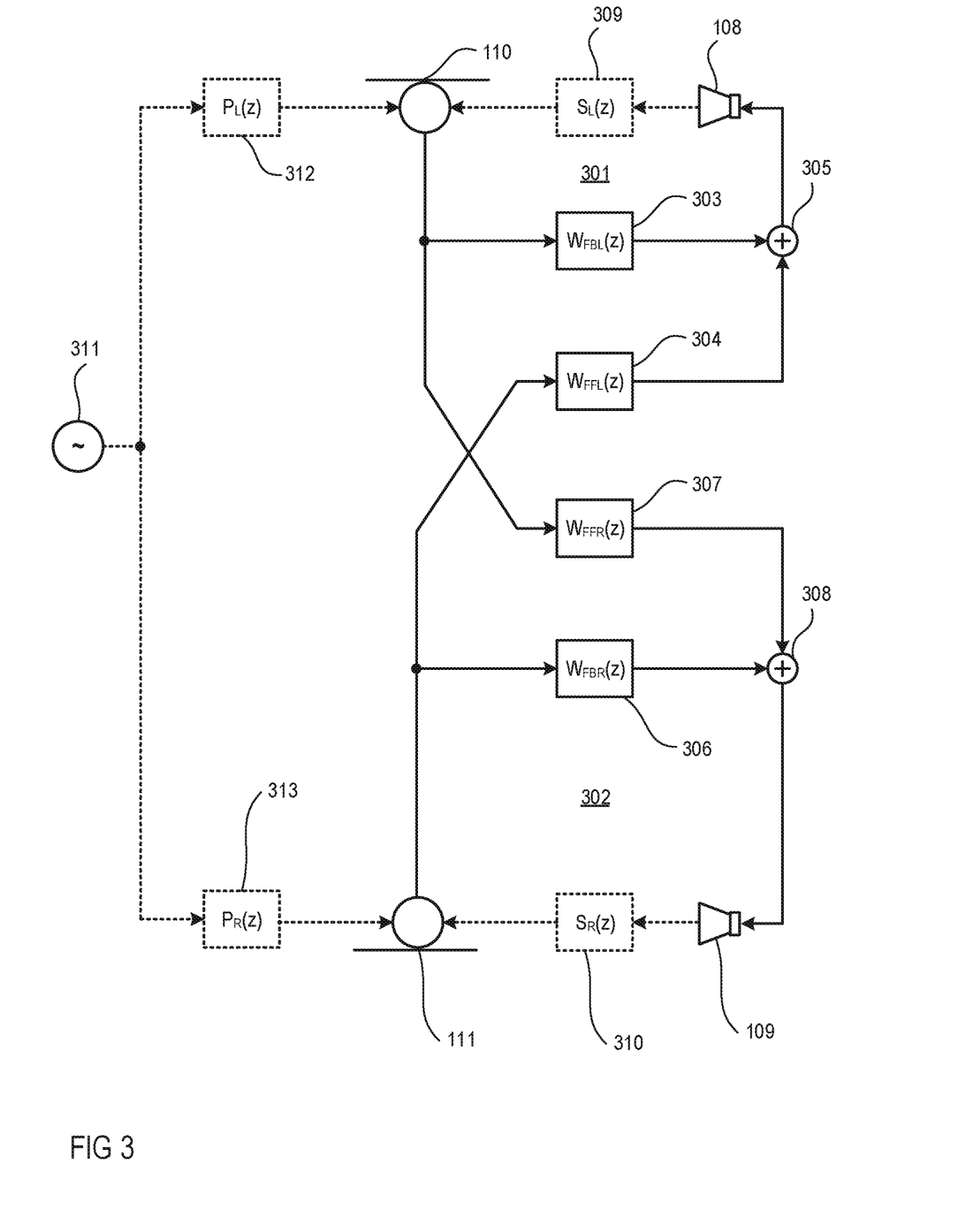
FIG. 3 is a block diagram of the exemplary active noise controller applicable in the helmet shown in FIGS. 1 and 2.

FIG. 3 shows an exemplary implementation of the active noise controller 112. The active noise controller 112 includes a left channel 301 and a right channel 302 which, in terms of signal processing structure, may be implemented identically and may be connected to loudspeakers 108 and 109, respectively. Channel 301 comprises a feedback filter 303 having a transfer function $W_{FBL}(z)$, a feed-forward filter 304 having a transfer function $W_{FFL}(z)$ and an adder 305 that adds signals output by the feedback filter 303 and the feed-forward filter 304. The input of feedback filter 303 serves as an error input and the input of feed-forward filter 304 serves as a reference input of the left channel 301 of active noise controller 112. Accordingly, the right channel 302 comprises a feedback filter 306 having a transfer function $W_{FBR}(z)$, a feed-forward filter 307 having a transfer function $W_{FFR}(z)$ and an adder 308 that adds signals output by the feedback filter 306 and the feed-forward filter 307. The input of feedback filter 306 serves as an error input and the input of feed-forward filter 307 serves as a reference input of the right channel 302 of active noise controller 112. A sum signal provided by adder 305 is supplied to loudspeaker 108 and a sum signal provided by adder 308 is supplied to loudspeaker 109. As can be seen, the outputs of the two channels 301 and 302 are electrically coupled to the two loudspeakers 108 and 109. The error-signal input of each channel 301,302 is electrically coupled to the microphone 110, 111 in the vicinity of the loudspeaker 108, 109 that is electrically coupled to the output of the same channel 301, 302, and the reference-signal input of each channel 301,302 is electrically coupled to the microphone 111, 110 in the vicinity of the loudspeaker 109, 108 that is electrically coupled to the output of the respective other channel 302, 301.

Furthermore, a microphone signal provided by microphone 110, which is close to loudspeaker 108, is supplied to feedback filter 303 and feed-forward filter 307, and a microphone signal provided by microphone 111, which is close to loudspeaker 109, is supplied to feedback filter 306 and feed-forward filter 304. Microphone 110 is acoustically linked to loudspeaker 108 via a secondary path 309 having a transfer function $S_L(z)$, and microphone 111 is acoustically linked to loudspeaker 109 via a secondary path 310 having a transfer function $S_R(z)$. The microphones 110 and 111 are further acoustically linked to a noise source 311 via a primary path 312 having a transfer function $P_L(z)$ and a primary path 313 having a transfer function $P_R(z)$. As can be seen, the microphones 110 and 111 are used such that they form crosswise the error microphone in one channel and the reference microphone in the other channel. The active noise controller 112 may include further elements such as amplifiers, filters etc. which are not shown in FIG. 3 for reasons of clarity and comprehensibility.

Figure 4:
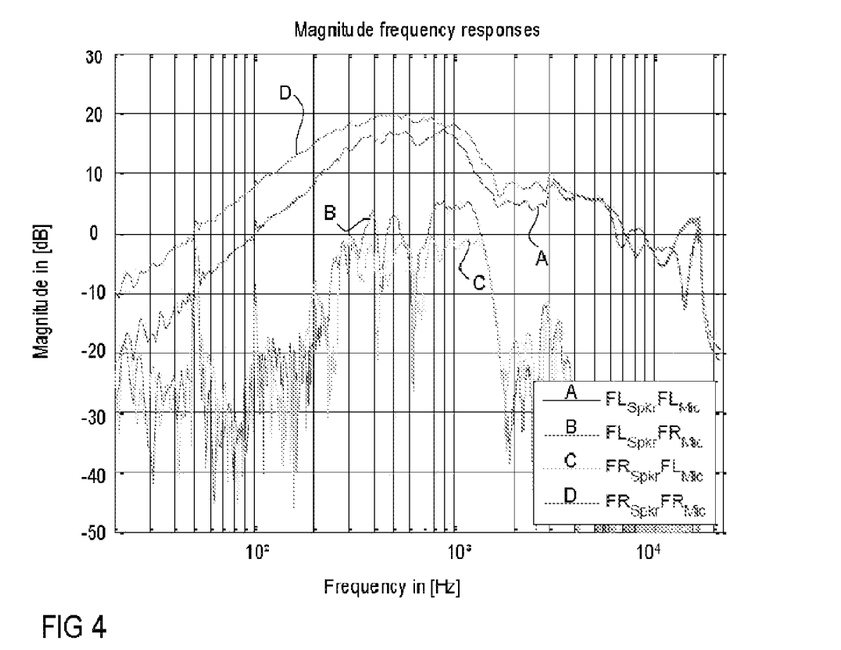
FIG. 4 is a diagram illustrating the magnitude frequency responses of an ANC helmet equipped with error microphones at the left and right side.
Figure 5:
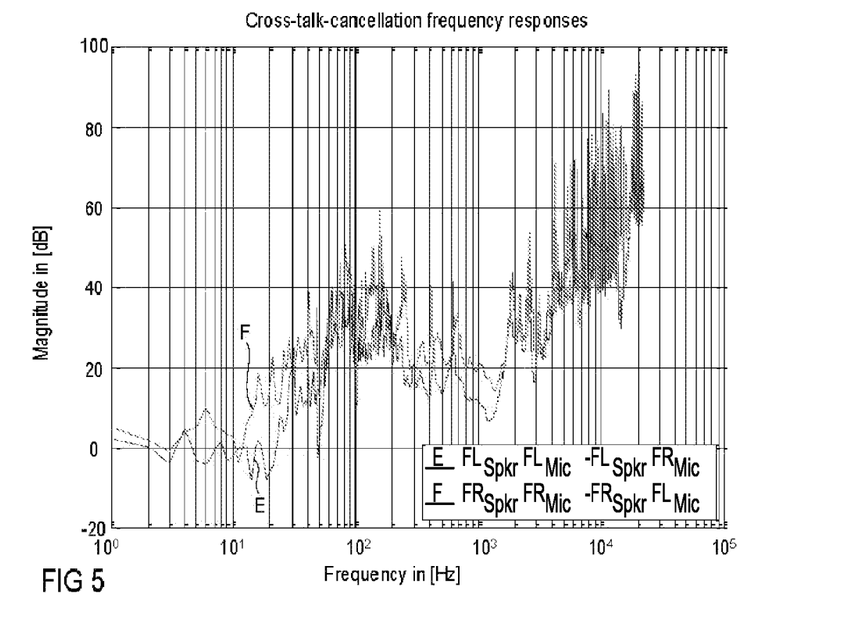
FIG. 5 is a diagram illustrating the cross-talk-cancellation (magnitude) frequency responses of an ANC helmet equipped with error microphones at the left and right side.

The performance of the helmet is similar to the helmet 100 but with no active noise control installed or active can be seen in FIG. 4, which is a diagram illustrating the magnitude frequency responses of the transmission paths between loudspeakers and error microphones and in an ANC helmet equipped with an error microphone $FL_{Mic}$ and a loudspeaker $FL_{Spkr}$ at the left, and an error microphone $FR_{Mic}$ and a loudspeaker $FR_{Spkr}$ at the right side. FIG. 5 is a diagram illustrating the corresponding cross-talk-cancellation (magnitude) frequency responses of such an ANC helmet.

Helmets may include ear-cups, which can be molded into the rigid portions of the helmet, such as the foam layer. The ear-cups may be static and merely provide space for a motorcyclist's ears, or they may include electronics, such as headphones, so that a motorcyclist may listen to music or communicate over an electronic communication system. In some cases, the ear-cups may be mounted to the shell of the helmet so that they can articulate and provide better comfort to motorcyclists. In other cases, the helmet may have a recess where a motorcyclist may install aftermarket ear-cups that are not a part of the helmet.

The ANC performance depends on how close the secondary paths match the situation based on which the ANC filter has been created. This means that best results can be achieved if the secondary paths can be reproduced independent of the wearing situation, thereby compensating natural deviations of the head or ears in size and/or form, i.e., if one wears glasses or has a beard, etc., and while still being able to match the trajectories of the reference secondary paths utilized for the creation of the ANC filter. Moreover, in ANC helmets, individual deviations are much higher as in case of, for example, closed headphones. Thus, keeping individual deviations in the secondary paths small is needed to achieve a sufficient ANC performance for a large variety of users. The better the helmet fits, the less individual deviations occur and the better (i.e., closer to the reference) the ANC performance will be.

This can be achieved by using, for example, memory material as (part of) the isolation layer, for example, as the foam layer 103 and/or the comfort layer 104, which guarantees a perfect fit independent of the size or form of the individual's ears or head, keeping individual variations in helmets small and thus the ANC performance high. Memory foam is, for example, polyurethane with additional chemicals increasing its viscosity and density. It is often referred to as "viscoelastic" polyurethane foam, or low-resilience polyurethane foam (LRPu). LRPu is a material that can be distinguished by an "ability to slowly return to its original shape." Memory foam softens in reaction to the head's heat, allowing it to mold to a warm head in a few minutes, however, exhibits a slow speed of recovery to its original shape after pressure is removed. Newer generations of memory foams have an open-cell structure that reacts faster to the head's heat and pressure by 'molding' to the head, helping relieve pressure points, preventing pressure sores, etc. Most memory foam has the same basic chemical composition, however the density and layer thickness of the foam makes different materials feel very different.

Figure 6:
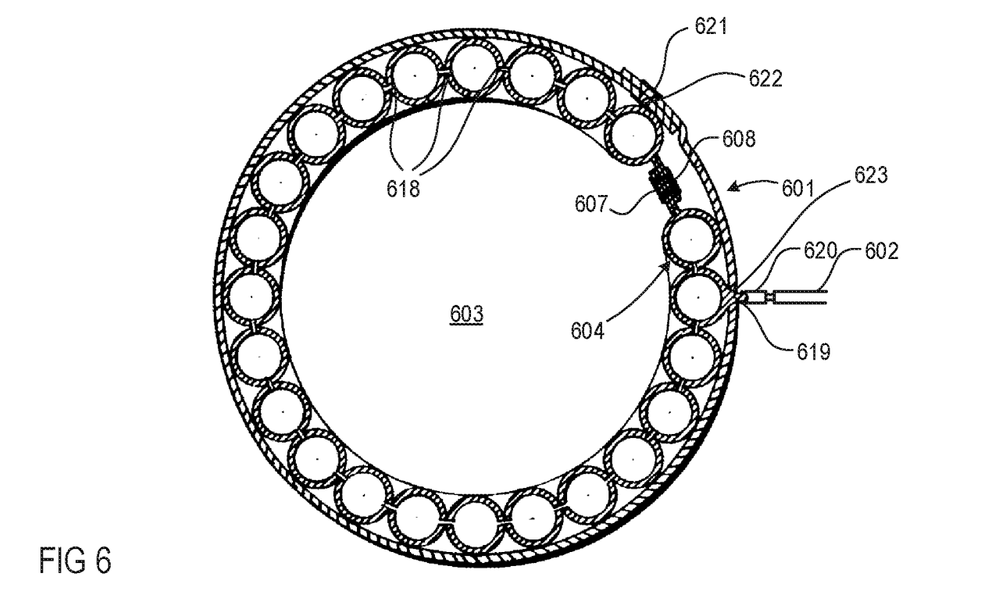
FIG. 6 is a cross-sectional view of an exemplary inflatable splint made from a pad.
Figure 7:
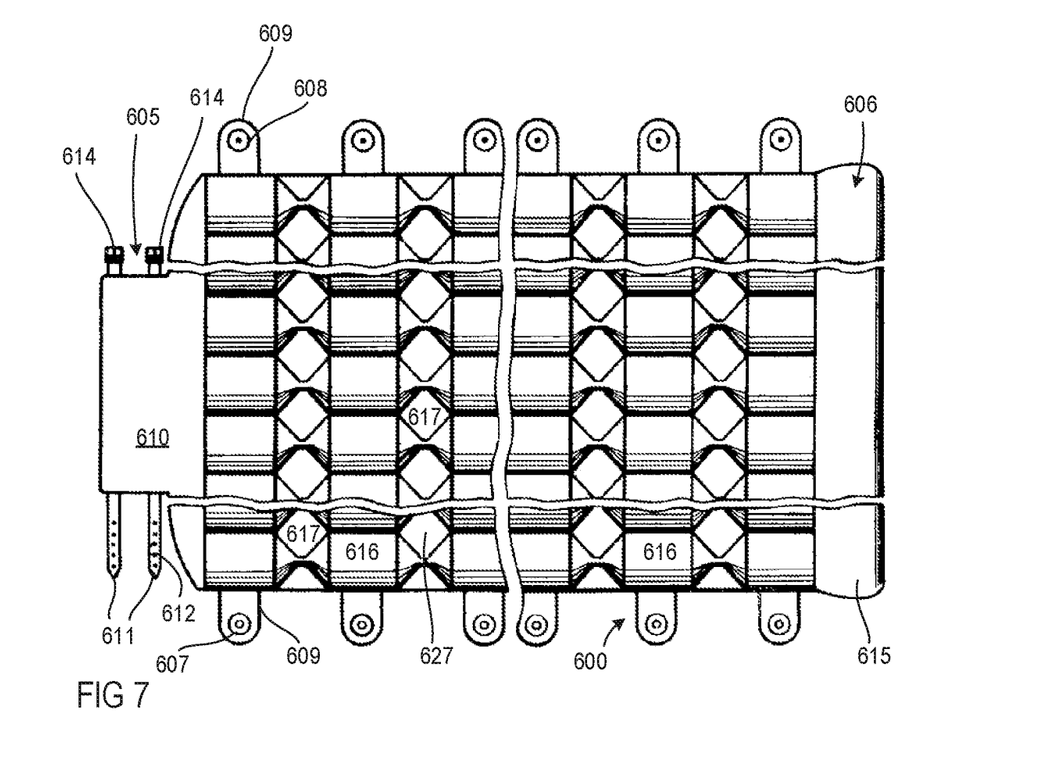
FIG. 7 is a top view illustrating the pad used in FIG. 6 in a flat or unfolded condition.

Additionally or alternatively to a memory foam layer, an inflatable splint for a helmet as shown in FIGS. 6 and 7, may be employed which may include an inflatable pad 600, a cover 601 for the pad 600, and an inlet 602 for effecting inflation of the pad 600 after being applied to a portion of a head 603 wearing the helmet. The pad 600 includes a plurality of lengthwise extending tubular flexible inflatable elements 604 arranged side-by-side, end connectors 605 and 606 for structurally connecting the elements 604 at their respective ends to provide a generally rectangular pad, and a plurality of lengthwise spaced, individually operable cooperating fasteners at the sides of the pad, such as cooperating male and female snap fasteners 607 and 608 on tabs 609 secured to the elements 604 at its respective sides. The end connector 605 may include a cult portion 610 secured to the elements 604 at one end thereof and a strap member 611 at opposite sides of the cuff portion, respectively provided with apertures 612 and buckles 614. The end connector 606 is in the form of an elongate pouch 615 for receiving the other end of the elements 604.

The tubular elements 604 may each be divided into a plurality of lengthwise extending cells 616 with adjacent cells of each element being connected for fluid flow communication at their ends by a restricted passageway 617, a row of side-by-side adjacent cells 616 are manifolded together for fluid flow communication by a passageway 618, and a cell of one element 604 in the manifolded row of cells is provided with a port 619 equipped with a suitable valve 620 for effecting inflation and deflation of the pad of cells. Preferably, for the reason to be stated hereinafter, the row of manifolded cells 616 is at about the midpoint between ends of the pad. The pad 600 as just described may be constructed of any material which lends itself to inflation by air or other compressed gases, such as rubber, rubberized fabric, and plastic resins. The fasteners 607, 608 and the buckles 614 preferably are formed of plastic resin.

The cover 601 is a rectangular sheet of fabric having rows of cooperating male and female snap fasteners 621 and 622 adjacent to its respective sides. The cover sheet 601 has a width to be wrapped about the pad 600 and fastened when the pad is applied to the head portion, and has a length greater than that of the pad so that portions at the ends of the cover sheet extend outwardly beyond the ends of the pad. These end portions are folded over the ends of the pad. The cover sheet may be formed with an opening 623 which is positioned to allow the port 619 to extend through it. Preferably, the cover sheet is formed of a porous fabric to allow air to pass through it, and the fasteners 621, 622 are formed of plastic resin. The inflating device 602 is illustrated herein as a squeezable bulb for producing air under pressure which is conducted through the valve 620 and the port 619 to effect inflation of the pad 600. However, it will be appreciated that other types of inflation devices, such as vessels containing gas under pressure, could be utilized.

In using the splint, the pad 600 may be fastened to the inner surface of the helmet (not shown) and as such wrapped around the head 603 when the helmet is worn. The pad 600 is then inflated to a desired pressure. The cover 601 now serves to restrict the outward swelling of the cells 616 and causes them to apply the desired pressure inwardly for fastening purposes and to longitudinally stiffen the pad. The spaces between lengthwise adjacent cells 616 provide openings 627 whereby air passing through the porous fabric cover sheet also passes through these openings to allow the splint to breathe and thus minimize skin irritation or other discomforts at the splinted head portion area.

Figure 8:
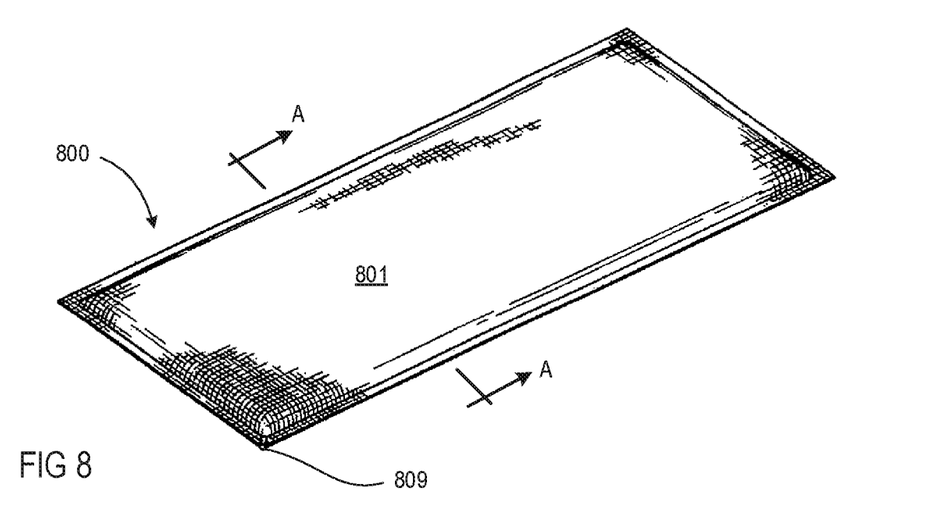
FIG. 8 is an isometric view of an air mattress being shown in an inflated condition for use.
Figure 9:
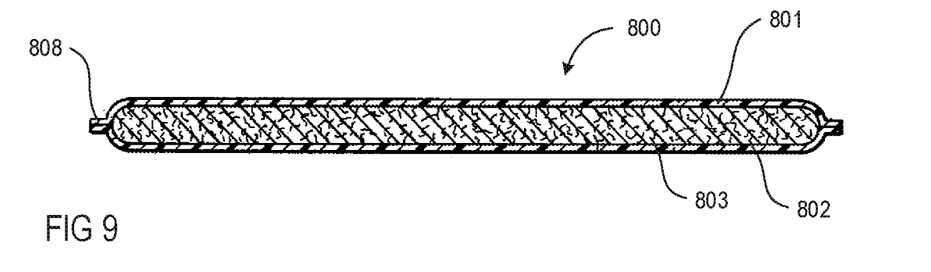
FIG. 9 is a transverse sectional view taken along line A-A of FIG. 8.
Figure 10:
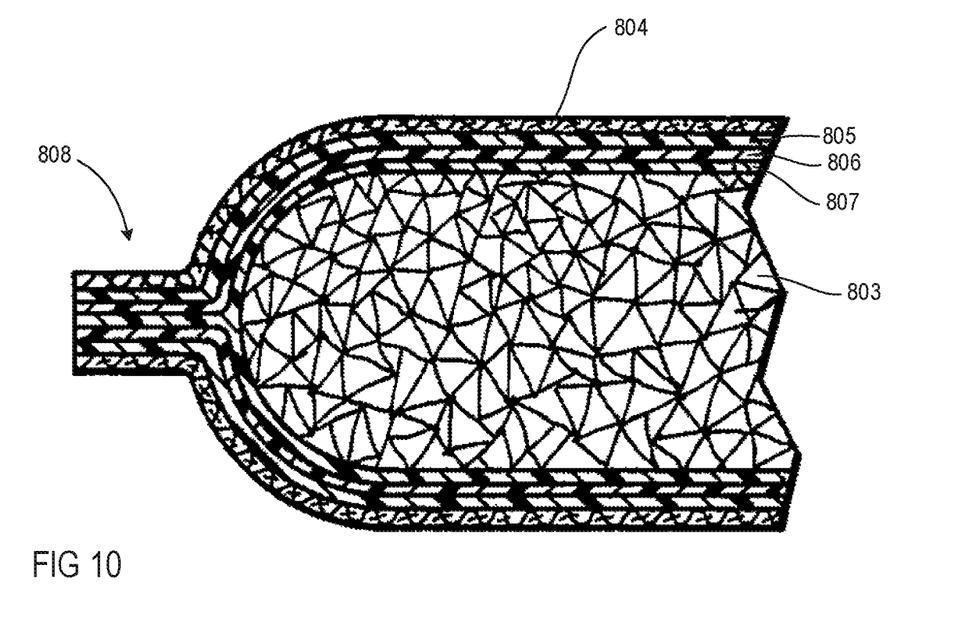
FIG. 10 is a sectional view, drawn to an enlarged scale, detailing the structure of the foam and the mattress envelope at the edge portion of the mattress.

With reference to FIGS. 8 and 9, another alternative may be an air cushion 800 which may be a flat, rectangular configuration and comprising upper and lower sheets or skin sections 801 and 802, respectively, which are bonded to one another about their entire perimeter to provide an air impervious envelope enclosing a core 803 of a lightweight, resilient, open cell foam material. As shown in FIG. 10, each of the sheets or skins 801 and 802 comprises an outer layer of a substantially non-stretchable fabric 804 made of nylon or some other stretch resistant material, next a base or tie layer to facilitate subsequent lamination to fabric 805, an impervious intermediate layer 806, and an innermost layer 807 of material to which the foam core 803 is bonded and which facilitates the peripheral bond. An edge joint or seal 808 at which the two sheets 801 and 802 are joined about their entire perimeter is made by bonding the two inner surfaces of the sheets 801 and 802 together about their entire perimeter to form a "T" joint or seam. There is a valve 809 comprising a thermoplastic polyurethane housing and a conventional valve member mounted therein. This valve 809 is bonded into one corner of the air cushion 800 during the manufacturing process. The air cushion 800 may be fastened to the inner surface of the helmet (not shown) and as such wrapped around a head (not shown) when the helmet is worn.

Figure 11:
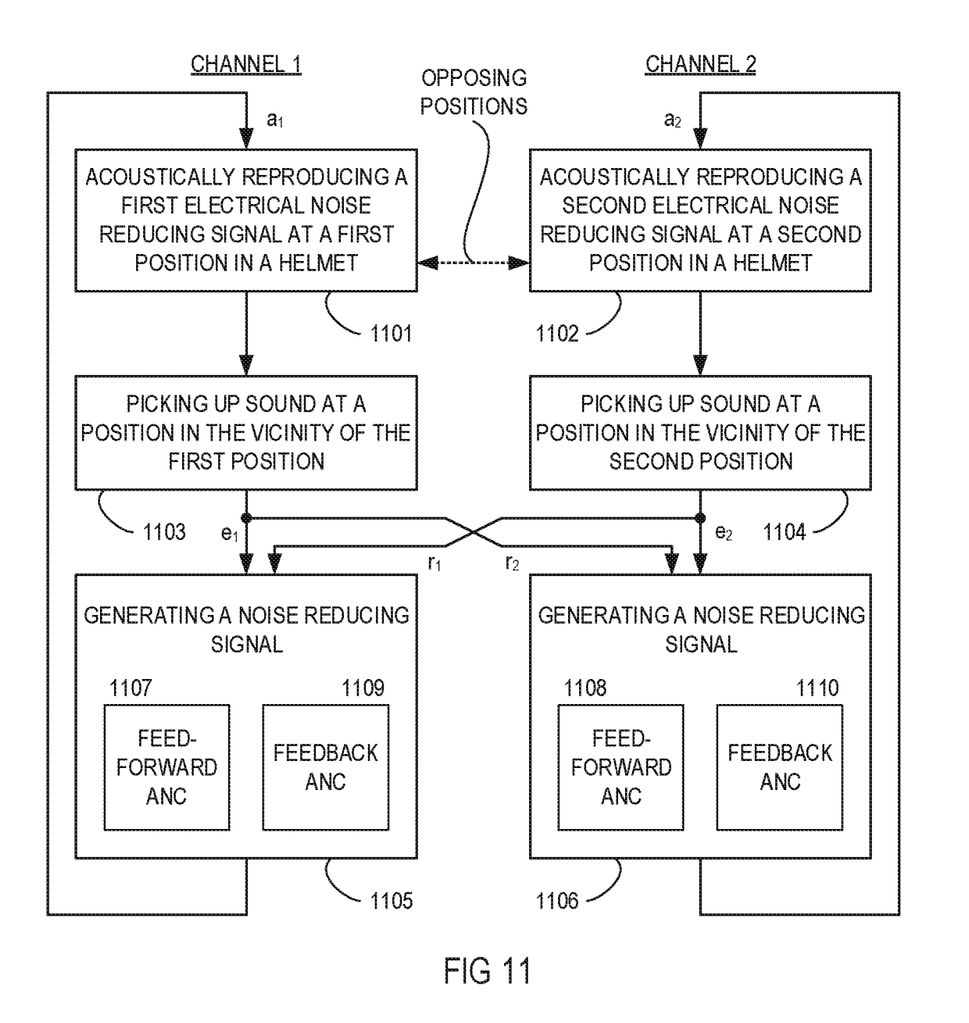
FIG. 11 is signal flow chart illustrating an exemplary noise reducing method applicable in a helmet.

FIG. 11 is signal flow chart illustrating an exemplary noise two-channel reducing method applicable in a helmet. The method includes acoustically reproducing two electrical noise reducing signals $a_1$ and $a_2$ at two opposing positions in a helmet (procedures 1101 and 1102). The method further includes picking up sound at positions in the vicinity of the positions where the noise reducing signals are reproduced (procedures 1103 and 1104) and generating the two noise reducing signals from error-signals $e_1$ and $e_2$ and reference-signals $r_1$ and $r_2$ (procedures 1105 and 1106), wherein, for each noise reducing signal, the corresponding error-signal $e_1$, $e_2$ is generated from the sound picked-up at the same position where the respective noise reducing signal $a_1$, $a_2$ is reproduced, and the reference-signal $r_1$, $r_2$ is generated from the sound picked-up at the position where the respective other noise reducing signal $a_2$, $a_1$ is reproduced, so that $e_1=r_2$ and $e_2=r_1$. Generating the two noise reducing signals may employ a two-channel combined feed-forward type and feedback type active noise reduction algorithm. Each channel may include feed-forward active noise control filtering (procedures 1107 and 1108) and feedback active noise control filtering (procedures 1109 and 1110). The feed-forward active noise control filtering may be based on the reference-signal of the respective channel, and the feedback active noise control filtering is based on the error-signal input of the respective channel.

The description of embodiments has been presented for purposes of illustration and description. Suitable modifications and variations to the embodiments may be performed in light of the above description. The described systems are exemplary in nature, and may include additional elements and/or omit elements. As used in this application, an element or step recited in the singular and proceeded with the word "a" or "an" should be understood as not excluding plural of said elements or steps, unless such exclusion is stated. Furthermore, references to "one embodiment" or "one example" of the present disclosure are not intended to be interpreted as excluding the existence of additional embodiments that also incorporate the recited features. The terms "first," "second," and "third," etc. are used merely as labels, and are not intended to impose numerical requirements or a particular positional order on their objects.

What is claimed is:

1. A noise reducing system comprising:
   a helmet;
   a first loudspeaker ($FL_{spkr}$) disposed in the helmet at an opposing position from a second loudspeaker ($FR_{spkr}$);
   a first microphone ($FL_{Mic}$) disposed in a vicinity of the first loudspeaker ($FL_{spkr}$) and a second microphone ($FR_{Mic}$) disposed in a vicinity of the second loudspeaker ($FR_{spkr}$); and
   an active noise controller including a processor and being operably coupled to the first loudspeaker ($FL_{spkr}$), the second loudspeaker ($FR_{spkr}$), the first microphone ($FL_{Mic}$), and the second microphone ($FR_{Mic}$) to perform active noise control;
   wherein a first magnitude frequency response is defined as being a product of a magnitude response of the first loudspeaker ($FL_{spkr}$) and a magnitude response of the first microphone ($FL_{Mic}$);
   wherein a second magnitude frequency response is defined as being a product of the magnitude response of the first loudspeaker ($FL_{spkr}$) and a magnitude response of the second microphone ($FR_{Mic}$);
   wherein the second magnitude frequency response is subtracted from the first magnitude frequency response to provide a third magnitude frequency response;
   wherein a fourth magnitude frequency response is defined as being a product of a magnitude response of the second loudspeaker ($FR_{spkr}$) and the magnitude response of the second microphone ($FR_{Mic}$);
   wherein a fifth magnitude frequency response is defined as being a product of the magnitude response of the second loudspeaker ($FR_{spkr}$) and the magnitude response of the first microphone ($FL_{Mic}$);
   wherein the fifth magnitude frequency response is subtracted from the fourth magnitude response to provide a sixth magnitude frequency response, and
   wherein the third magnitude frequency response at least partially overlaps with the sixth magnitude response when the active noise controller is activated.

2. The system of claim 1, wherein the helmet comprises a shell and an isolation layer; wherein the isolation layer is disposed in the shell and has a first receptable and a second receptable at opposing positions; and the first loudspeaker ($FL_{spkr}$) is disposed in the first receptable and the second loudspeaker ($FR_{spkr}$) is disposed in the second receptable.

3. The system of claim 2, wherein
   the shell has a front opening; and
   the first microphone ($FL_{mic}$) is disposed between the front opening and the first loudspeaker ($FL_{spkr}$); and
   the second microphone ($FR_{mic}$) is disposed between the front opening and the second loudspeaker ($FR_{spkr}$).

4. The system of claim 1, wherein the active noise control controller is of a combined feed-forward and feedback type.

5. The system of claim 1, wherein the helmet includes an isolation layer having memory foam.

6. The system claim 5, wherein the isolation layer includes a deflating vacuum cushion.

7. The system of claim 5, wherein the isolation layer includes an inflatable splint.

8. The system of claim 1, wherein the first microphone ($FL_{mic}$) and the second microphone ($FR_{mic}$) are disposed inside the helmet at a same curved plane as the first loudspeaker ($FL_{spkr}$) and the second loudspeaker ($FR_{spkr}$), respectively, such that first microphone ($FL_{mic}$) and the second microphone ($FR_{mic}$) are arranged to face a front side opening of the helmet in a direction where a noise source resides.

9. A noise reducing method comprising:
   acoustically reproducing two electrical noise reducing signals at two opposing positions in a helmet with a first loudspeaker ($FL_{spkr}$) and a second loudspeaker ($FR_{spkr}$); and picking up sound at positions in a vicinity of where the noise reducing signals are reproduced with a first microphone ($FL_{Mic}$) and a second microphone ($FR_{Mic}$);

wherein the first microphone ($FL_{Mic}$) and the second microphone ($FR_{Mic}$) are disposed inside the helmet such that the first microphone ($FL_{Mic}$) and the second microphone ($FR_{Mic}$) are arranged to face an opening of the helmet, wherein a first magnitude frequency response is defined as being a product of a magnitude response of the first loudspeaker ($FL_{spkr}$) and a magnitude response of the first microphone ($FL_{Mic}$);

wherein a second magnitude frequency response is defined as being a product of the magnitude response of the first loudspeaker ($FL_{spkr}$) and a magnitude response of the second microphone ($FR_{Mic}$);

wherein the second magnitude frequency response is subtracted from the first magnitude frequency response to provide a third magnitude frequency response;

wherein a fourth magnitude frequency response is defined as being a product of a magnitude response of the second loudspeaker ($FR_{spkr}$) and the magnitude response of the second microphone ($FR_{Mic}$);

wherein a fifth magnitude frequency response is defined as being a product of the magnitude response of the second loudspeaker ($FR_{spkr}$) and the magnitude response of the first microphone ($FL_{Mic}$);

wherein the fifth magnitude frequency response is subtracted from the fourth magnitude response to provide a sixth magnitude frequency response, and wherein the third magnitude frequency response at least partially overlaps with the sixth magnitude response when the operation of acoustically reproducing two electrical noise reducing signals is activated.

10. The method of claim 9, wherein generating the two electrical noise reducing signals employs a two-channel combined feed-forward and feedback type active noise reduction algorithm.

11. The method of claim 9, wherein the first microphone ($FL_{mic}$) and the second microphone ($FR_{mic}$) are disposed inside the helmet at a same curved plane as the first loudspeaker ($FL_{spkr}$) and the second loudspeaker ($FR_{mic}$), respectively, such that first microphone ($FL_{mic}$) and the second microphone ($FR_{mic}$) are arranged to face a front side opening of the helmet in a direction where a noise source resides.

12. A noise reducing system comprising:
a helmet;
a first loudspeaker ($FL_{spkr}$) and a second loudspeaker ($FR_{spkr}$), each of the first loudspeaker ($FL_{spkr}$) and the second loudspeaker ($FR_{spkr}$) are positioned in the helmet at opposing positions from one another;
a first microphone ($FL_{Mic}$) disposed in a vicinity of the first loudspeaker ($FL_{spkr}$);
a second microphone ($FR_{Mic}$) disposed in a vicinity of the second microphone ($FR_{spkr}$); and an active noise controller including a processor and two channels each with an error-signal input, a reference-signal input and an output;

wherein a first magnitude frequency response is defined as being a product of a magnitude response of the first loudspeaker ($FL_{spkr}$) and a magnitude response of the first microphone ($FL_{Mic}$);

wherein a second magnitude frequency response is defined as being a product of the magnitude response of the first loudspeaker ($FL_{spkr}$) and a magnitude response of the second microphone ($FR_{Mic}$);

wherein the second magnitude frequency response is subtracted from the first magnitude frequency response to provide a third magnitude frequency response;

wherein a fourth magnitude frequency response is defined as being a product of a magnitude response of the second loudspeaker ($FR_{spkr}$) and the magnitude response of the second microphone ($FR_{Mic}$);

wherein a fifth magnitude frequency response is defined as being a product of the magnitude response of the second loudspeaker ($FR_{spkr}$) and the magnitude response of the first microphone ($FL_{mic}$);

wherein the fifth magnitude frequency response is subtracted from the fourth magnitude response to provide a sixth magnitude frequency response, and wherein the third magnitude frequency response at least partially overlaps with the sixth magnitude response when the active noise controller is activated.

13. The system of claim 12, wherein the helmet comprises a shell and an isolation layer, wherein the isolation layer is disposed in the shell and includes two receptacles at opposing positions; and the first loudspeaker ($FL_{spkr}$) is disposed in one of the two receptacles and the second loudspeaker ($FR_{spkr}$) is disposed in another of the two receptacles.

14. The system of claim 13, wherein
the shell includes a front opening;
the first microphone ($FL_{mic}$) is disposed between the front opening and the first loudspeaker ($FL_{mic}$) ; and
the second microphone ($FR_{mic}$) is disposed between the front opening and the second loudspeaker ($FR_{mic}$).

15. The system of claim 12, wherein the active noise controller is of a combined feed-forward and feedback type.

16. The system of claim 12, wherein the helmet includes an isolation layer having memory foam.

17. The system claim 16, wherein the isolation layer includes a deflating vacuum cushion.

18. The system of claim 16, wherein the isolation layer includes an inflatable splint.

19. The system of claim 12, wherein the first microphone ($FL_{mic}$) and the second microphone ($FR_{mic}$) are disposed inside the helmet at a same curved plane as the first loudspeaker ($FL_{spkr}$) and the second loudspeaker ($FR_{spkr}$) , respectively, such that first microphone ($FL_{mic}$) and the second microphone ($FR_{mic}$) are arranged to face a front side opening of the helmet in a direction where a noise source resides.

* * * * *